United States Patent
Kirwan, Jr.

(10) Patent No.: US 6,298,550 B1
(45) Date of Patent: Oct. 9, 2001

(54) PROCESS FOR MANUFACTURING ELECTRO-SURGICAL FORCEPS WHICH MINIMIZES OR PREVENTS STICKING OF TISSUE

(75) Inventor: Lawrence T. Kirwan, Jr., Pembroke, MA (US)

(73) Assignee: Kirwan Surgical Products, Inc., Marshfield, MA (US)

( * ) Notice: Subject to any disclaimer, the term of this patent is extended or adjusted under 35 U.S.C. 154(b) by 0 days.

(21) Appl. No.: 09/362,967

(22) Filed: Jul. 29, 1999

Related U.S. Application Data

(62) Division of application No. 09/102,065, filed on Jun. 22, 1998.
(60) Provisional application No. 60/050,880, filed on Jun. 26, 1997.

(51) Int. Cl.⁷ ..................................................... H01R 43/00
(52) U.S. Cl. ............................... 29/825; 606/48; 606/51; 606/52
(58) Field of Search ................................ 29/825; 606/45, 606/48, 57, 52

(56) References Cited

U.S. PATENT DOCUMENTS

| | | | |
|---|---|---|---|
| 4,492,231 | 1/1985 | Auth | 128/303.17 |
| 5,196,009 | 3/1993 | Kirwan, Jr. | 606/51 |
| 5,951,549 | * 9/1999 | Richardson et al. | |
| 5,976,132 | * 11/1999 | Morris | |
| 6,050,996 | * 4/2000 | Schmaltz et al. | |
| 6,090,108 | * 7/2000 | McBrayer et al. | |
| 6,174,309 | * 1/2001 | Wrublewski et al. | |
| 6,176,866 | * 1/2001 | Christoudias | |
| 6,179,837 | * 1/2001 | Hooven | |
| 6,187,003 | * 2/2001 | Buysse et al. | |
| 6,193,718 | * 2/2001 | Kortenbach et al. | |
| 6,223,440 | * 5/2001 | Rashman | |
| 6,238,391 | * 5/2001 | Olsen et al. | |

\* cited by examiner

Primary Examiner—Carl J. Arbes
(74) Attorney, Agent, or Firm—Weingarten, Schurgin, Gagnebin & Hayes LLP

(57) ABSTRACT

An electro-surgical forceps are provided which minimize sticking to tissue of a patient. The forceps include a pair of electrically conducting blade members extending from an insulated cap portion. The blade members include an inner layer of copper or copper alloy having a thickness sufficient to dissipate heat generated at the tip to prevent sticking of tissue to the forceps during use. An outer covering of nickel or a nickel alloy covers the inner copper layer to prevent exposure of the copper. The outer covering comprises a first nickel layer metallurgically bonded to one side of the inner copper layer and a second nickel layer metallurgically bonded to an opposite side of the inner copper layer. The thickness of the nickel layers is sufficient to withstand the forming process, to minimize or prevent delamination from the inner copper layer, and to minimize or prevent exposure of the inner layer.

3 Claims, 3 Drawing Sheets

PROCESS FOR MANUFACTURING ELECTRO-SURGICAL FORCEPS WHICH MINIMIZES OR PREVENTS STICKING OF TISSUE

CROSS REFERENCE TO RELATED APPLICATIONS

This application claims the benefit under 35 U.S.C. §119 (e) of U.S. application Ser. No. 60/050,880, filed on Jun. 26, 1997, and is a Division 35 U.S.C. §120 of U.S. application Ser. No. 09/102,065, filed on Jun. 22, 1998, the disclosures of which are incorporated by reference herein.

STATEMENT REGARDING FEDERALLY SPONSORED RESEARCH OR DEVELOPMENT

N/A

BACKGROUND OF THE INVENTION

Electro-surgical forceps have a pair of resilient blades or arms which are used for grasping and coagulating tissue. The forceps may be monopolar or bipolar. In monopolar forceps, the blades are welded or otherwise joined to form an electrode in electrical communication with an electrical generator. Current flows from the active electrode through the patient's tissue to a dispersive electrode in contact with the patient's skin (which may be at some distance from the forceps) and back to the generator. In bipolar forceps, each blade of the pair comprises an electrode in communication with an electrical generator. Current flows from one blade through the tissue to the other blade.

In some instances, tissue may adhere or stick to the tips of the blades. If sticking occurs, the surgeon must pull on the forceps to release it from the tissue, possibly causing further bleeding and requiring that the forceps be cleaned. It is known to prevent or minimize such sticking of tissue to electrosurgical forceps by manufacturing the blades of the forceps from nickel. See, for example, U.S. Pat. No. 5,196,009. During high power operation, some eschar buildup and some sticking of the tissue to the tips still may occur. Another known manner of preventing or minimizing sticking is to form the blades from a metal or metal alloy having a relatively high thermal conductivity, such as copper, which is able to transfer heat away from the tips of the blades. By keeping the tissue cooler, for example, below the boiling point of water, coagulation is able to occur without sticking of the tissue. See, for example, U.S. Pat. No. 4,492,231.

BRIEF SUMMARY OF THE INVENTION

An electro-surgical forceps are provided which minimize or prevent sticking to the tissue of a patient and eschar buildup. The forceps include a pair of blade members extending from an insulated cap portion. At least one of the blade members is electrically conducting. Within the cap portion, the blades are electrically connected to terminals for connection to an electrical generator.

The blade members include an inner layer of copper or copper alloy having a thickness sufficient to dissipate heat generated at the tip to prevent sticking of tissue to the forceps during use and to allow operation of the forceps at a lower power level. An outer covering of a strong, biocompatible metal or metal alloy covers the surfaces of the inner copper layer to prevent exposure of the copper. Preferably, the outer covering comprises a first nickel layer metallurgically bonded to one side of the inner copper layer and a second nickel layer metallurgically bonded to an opposite side of the inner copper layer. The thickness of the nickel layers is sufficient to withstand the forming process, to minimize or prevent delamination from the inner copper layer, and to minimize or prevent exposure of the inner copper layer through the nickel layers.

An insulating material is provided over the blade members from the cap portion to a location adjacent the tip of the blade member. A biocompatible plating, typically of gold, preferably encapsulates the tip to provide additional electrical and thermal conductivity and additional coverage of the inner copper layer on the edges.

The nickel layers are more biocompatible with human tissue than copper and are thus preferable for contact with the tissue, as well as providing additional non-stick capabilities. Also, the nickel layers have a thickness significantly greater than the thickness of a coating formed by a plating process. This greater thickness ensures that the nickel layers are able to withstand the forming process and are unlikely to wear away through use or during cleaning of the forceps, as is the case with a plating. Also, the process of metallurgically bonding the nickel layers to the copper layer of the present invention further minimizes the likelihood that the nickel layers may delaminate or separate from the copper layer. Further, nickel or nickel alloys are hard metals which also render them suitable for withstanding the forming process of the present invention and for providing a wear resistant outer covering.

DESCRIPTION OF THE DRAWINGS

The invention will be more fully understood from the following detailed description taken in conjunction with the accompanying drawings in which.

DETAILED DESCRIPTION OF THE INVENTION

Figure 1:
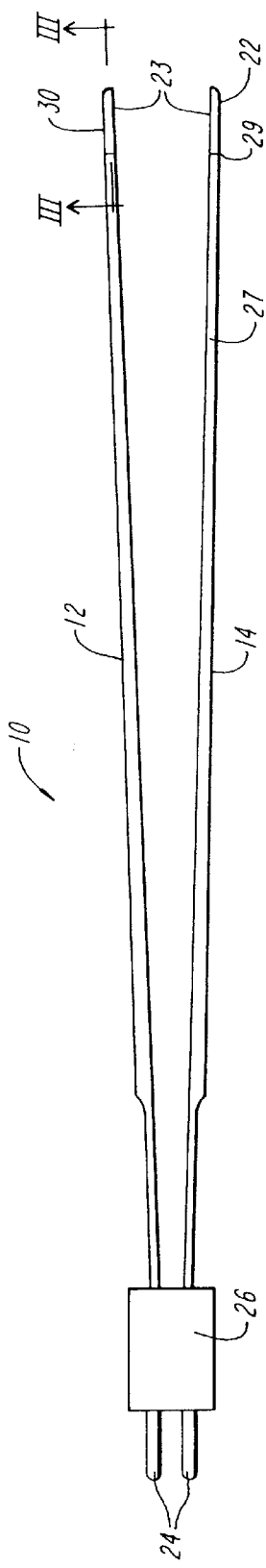
FIG. 1 is a side view of electro-surgical forceps according to the present invention.

Referring to FIGS. 1–5, a bipolar forceps 10 has first and second blade or electrode members 12 and 14. Each of the blade members are elongated and extend from a first end 20 to a second end or tip 22. The blades are generally flat to have a greater width than depth, such that the tips are configured for gripping tissue between opposed surfaces 23. First ends 20 are electrically connected in any suitable manner, such as by crimping, welding, or soldering, to terminal pins 24. First ends 20 along with the terminal pins 24 are encapsulated using an epoxy based material or otherwise mounted within an insulating cap portion 26. The blades are insulated with an insulating material 27 along most of their length from the cap portion 26 to a location 29 close to the tip. Serrated finger grips 31 may be formed in each blade member to aid the physician in gripping the forceps during use. A plating 28 of an electrically and thermally conductive biocompatible material such as gold may be provided on the tip 22.

Figure 3:
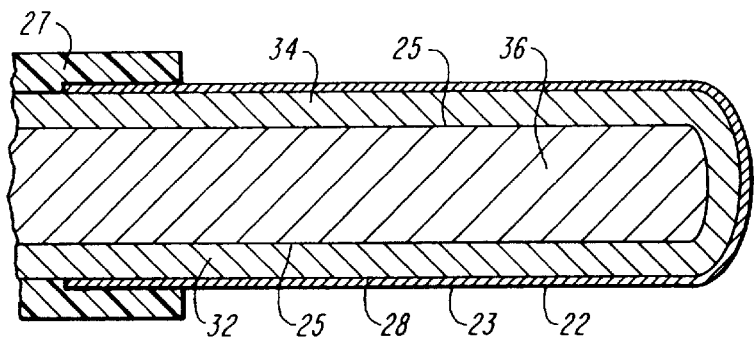
FIG. 3 is a cross-sectional view along line III—III of FIG. 1.
Figure 4:
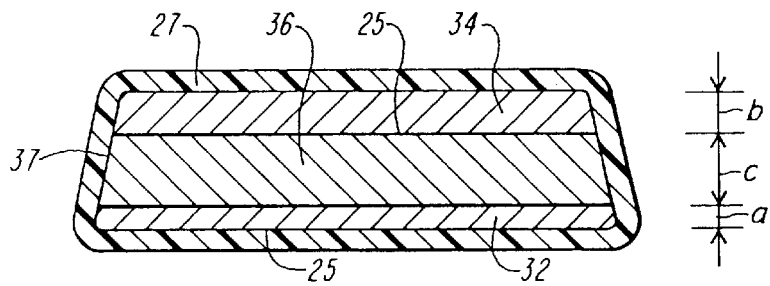
FIG. 4 is a cross-sectional view along line IV—IV of FIG. 2.
Figure 5:
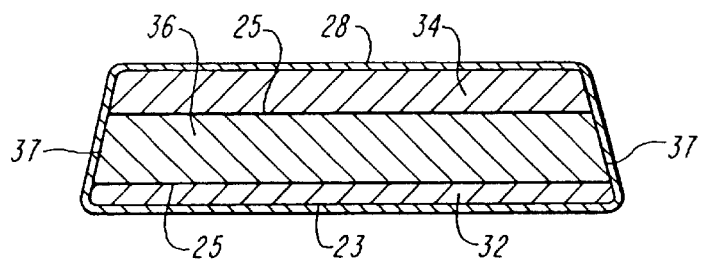
FIG. 5 is a cross-sectional view along line V—V of FIG. 2.

Referring more particularly to FIGS. 3 through 5, at least one and preferably both of the blade members 12 and 14 comprise a multi-layered structure having an inner copper layer 36 covered with an outer covering of nickel layers 32, 34 which fully cover the surfaces 25 of the copper layer. The outer nickel layers should be sufficiently thick to prevent exposure of the underlying copper layer during the forming operation in which the edge 48 (see FIG. 7) of the forceps is rounded, discussed further below, and to minimize or prevent exposure of the copper layer by wear of the nickel layer during use or cleaning of the forceps. The nickel layers may also cover the sides 37 of the copper layer if desired, although this is not necessary for satisfactory operation of the forceps. The outer nickel layers 32, 34 may be of the same or of different thicknesses. If it is desired to minimize nickel usage, the nickel layer may be slightly thinner on the side of the outwardly facing surface 30 than on the side of the grasping surface 23 which contacts the tissue. In the preferred embodiment, the thicknesses a and b of the outer nickel layers 32, 34 range from approximately 0.010 to approximately 0.050 inches. The thickness of the inner copper layer c ranges from approximately 0.030 to approximately 0.090 inches. In one embodiment, the thicknesses a and b of the outer nickel layers 32, 34 are approximately 0.030 and 0.015 inches, respectively, while the thickness c of the inner copper layer is approximately 0.045 inches.

The inner copper layer 36 may be made from pure copper or a variety of copper alloys. Generally, the copper alloy should contain at least 85% copper. Preferably, the inner copper layer 36 is made from CDA 102 half-hard. The outer nickel layers 32, 34 may be made from pure nickel or a variety of nickel alloys. Generally, the nickel alloy should contain at least 85% nickel. Preferably, the outer nickel layers 32, 34 are made from a Nickel 200 series, which is considered commercially pure, containing at least 99% nickel.

Figure 6:
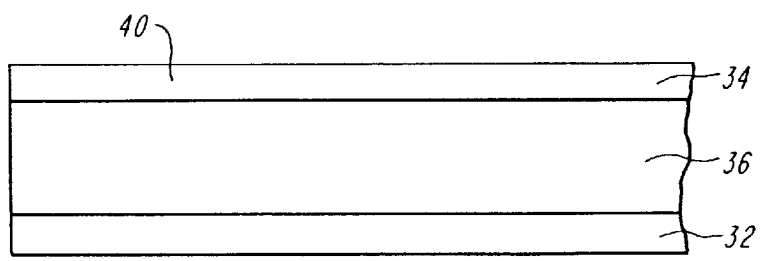
FIG. 6 is a partial view of a tri-laminate sheet for use in manufacturing the forceps according to the present invention.

Referring to FIG. 6, the inner copper layer 36 and the outer nickel layers 32, 34 are preferably made from strip stock bonded together to form a tri-laminate sheet 40 using a bonding process such as cold bonding under high pressure to create a metallurgical bond between the layers. This process begins with components of strip stock which are thicker than the final dimensions of the product. Each component is cleaned and cold bonded in a rolling mill, reducing the thickness and bonding the components together. Although referred to as "cold" bonding, the temperature of the material exiting the mill is typically greater than 300 to 400° F.; the temperatures of hot bonding techniques, however, are typically greater than 1000° F. At this stage, the material is in a green bonded state. The material is then annealed to create a metallurgical bond between the layers. With this bond, the material fractures before the layers separate.

Figure 2:
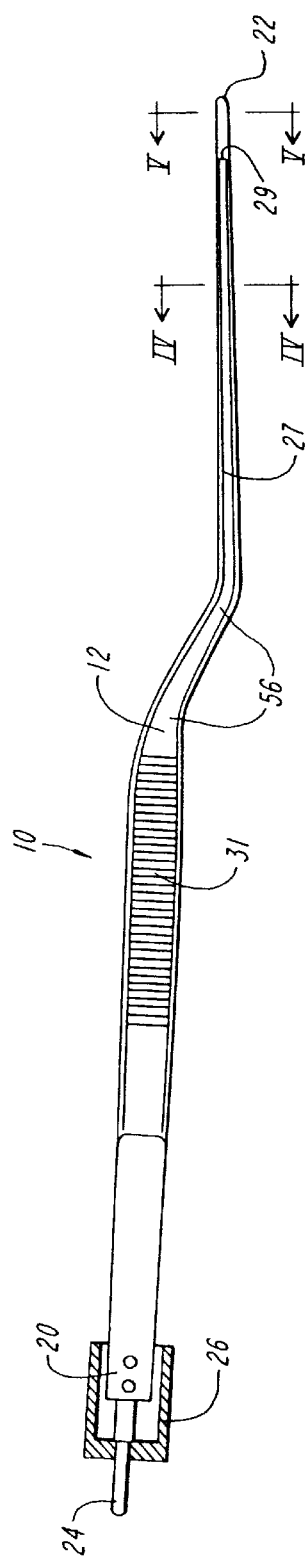
FIG. 2 is a plan view of the forceps of FIG. 1.
Figure 7:
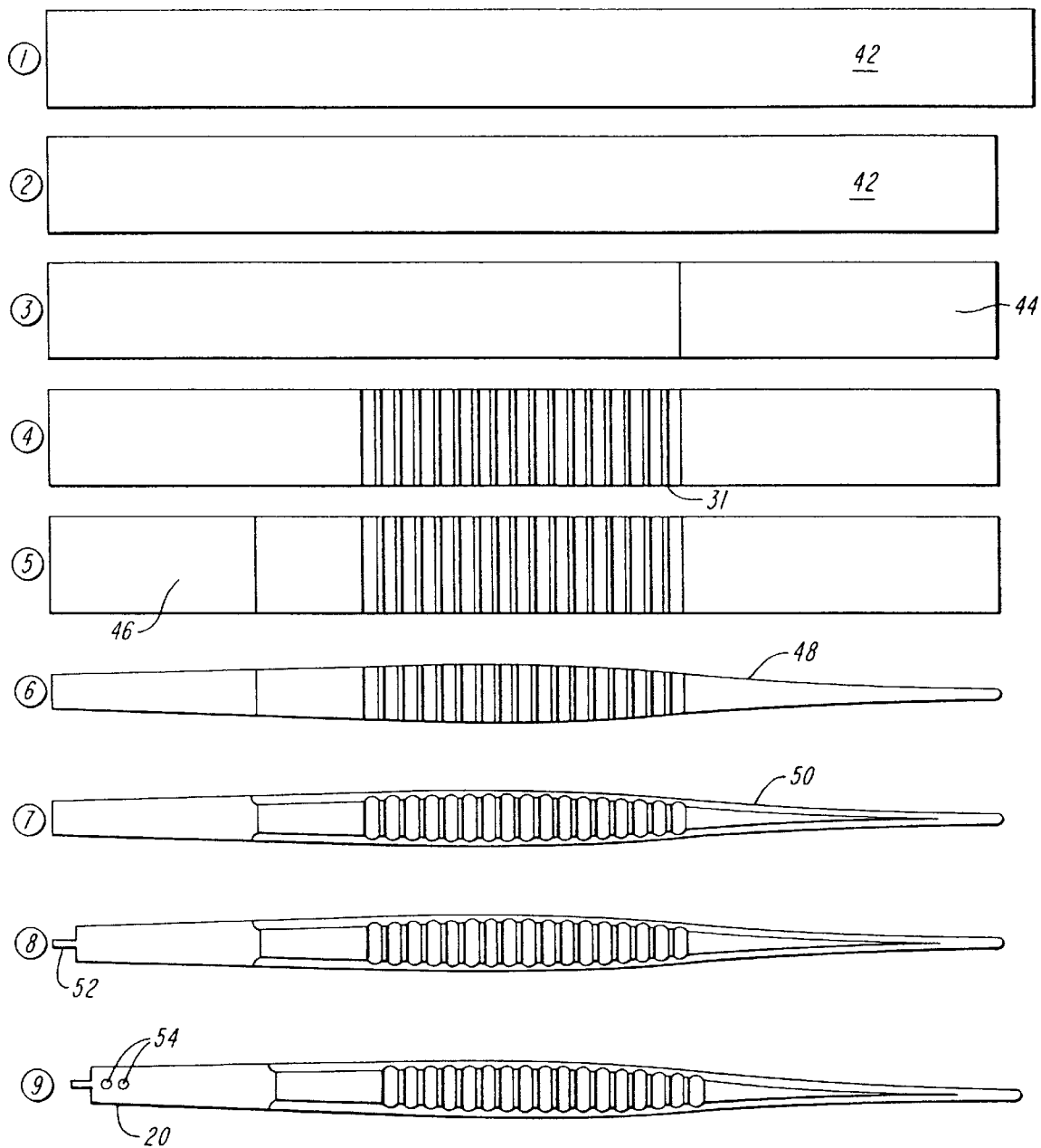
FIG. 7 is a diagrammatic view of steps in a process of manufacturing the forceps according to the present invention.

FIG. 7 illustrates representative steps in the process of manufacturing a blade member according to the invention. In step 1, the tri-laminate sheet is cut into strips 42, and in step 2, the strips are cut to the appropriate length for a blade member. A taper 44 is stamped at one end of the strip for the tip of the blade member in step 3. Serrations are stamped into a mid portion of the strip in step 4. In step 5, the rear or spring section 46 is cold formed, as by rolling, to compress its thickness and to work harden the material. Work hardening of the material in this section strengthens the material, enabling a physician to squeeze the blades together repeatedly to grasp tissue and release the blades to return to their rest position. The perimeter 48 of the strip is stamped to form the general shape of the blade member in step 6. As indicated in FIG. 7, the blade member could have a generally straight configuration, or as indicated in FIG. 2, the blade member could have bends 56 along its length, depending on the particular application. In step 7, the perimeter of the blade member is formed, as by a coining process, to form the edges 37.

A tab 52 is stamped, deburred, and formed at the end of the blade member in step 8. The terminal pins 24 may be attached to the tabs 52 in any suitable manner, such as by crimping, welding, or soldering. Holes 54 may be stamped into the end in step 9. The holes allow epoxy or other appropriate potting material to flow through and around the blades to fix the blades more firmly within the cap portion.

Preferably, the tip 22 is plated with a thin layer 28 of an electrically and thermally conducting, biocompatible material, such as gold, using conventional plating processes. For example, the thickness of the layer 28 generally ranges from 0.0001 to 0.001 inches, and is typically about 0.0004 inches. Because the nickel layers may not cover the copper layer fully along the edges 37, the plating also provides coverage of the inner copper layer in this region. The gold layer 28 provides good electrical and thermal conductivity. The gold layer 28 may be made from a variety of gold alloys. Preferably, the gold layer 28 is made from 24 carat hard gold. Other electrically and thermally conductive materials which are biocompatible with human tissue may be used.

The blade member is then encapsulated in insulating material 27, such as a plastic material capable of withstanding the high temperatures generated during use. The insulation may be formed in any suitable manner, such as by spraying on a liquid which dries to form a solid coating. The tip 22 of the blade member is left uninsulated for a suitable distance, such as ⅜ inch. The insulation is typically 0.010 to 0.015 inches thick.

The inner copper layer 36 within the blade members increases dissipation of heat generated at the tips 22 during use, thereby reducing the tendency of the tissue to stick to the tips 22 and allowing operation of the forceps at a lesser power level. The nickel layers are more biocompatible with human tissue than copper and are thus preferable for contact with the tissue, as well as providing additional non-stick capabilities. Additionally, the nickel layers have a thickness significantly greater than the thickness of a coating formed by a plating process. A plating process provides coatings typically on the order of microns or of thousands of an inch, whereas the nickel layers of the present invention are at least on the order of ten times and preferably on the order of one hundred times this thickness. This greater thickness ensures that the nickel layers are able to withstand the forming process and are unlikely to wear away through use or during cleaning of the forceps, as is the case with a plating. Also, the process of metallurgically bonding the nickel layers to the copper layer further minimizes the likelihood that the nickel layers may delaminate or separate from the copper layer during use or cleaning. Additionally, nickel is sufficiently strong to withstand the forming processes used in the manufacture of the blade members.

Although the invention has been particularly described with respect to bipolar forceps, it will be appreciated that the invention is equally applicable to monopolar forceps. Additionally, although it is preferable that both blades of the forceps be formed with the tri-laminate structure described above, only one blade could be so formed if desired.

Although the outer covering has been described as comprising layers of a nickel or nickel alloy, other suitable hard, biocompatible metals or metal alloys such as gold could be used for the outer covering if desired. The invention is not to be limited by what has been particularly shown and described, except as indicated by the appended claims.

I claim:

1. A process for manufacturing an electro-surgical forceps comprising:

bonding a first layer of nickel or a nickel alloy to an upper surface of a layer of copper or a copper alloy and a second layer of nickel or a nickel alloy to a lower surface of the layer of copper or copper alloy to form a tri-laminate sheet;

cutting the tri-laminate sheet into a strip having a width and length suitable for forming a forceps blade member;

stamping a taper at one end of the strip to form a tip of the blade member;

stamping a perimeter of the strip to form the general shape of the blade member;

deforming the first and second layers of the nickel or nickel alloy about the perimeter to fully encapsulate the layer of copper or copper alloy;

forming an end of the strip opposite the tip for connection to an electrode;

providing an insulating material over the strip from a location adjacent the tip to the opposite end;

providing a second blade member;

connecting the blade member and the second blade member to electrodes at a connection; and fixing the connection between the blade member, the second blade member, and the electrodes within an insulating cap portion.

2. The process of claim 1, further comprising plating an electrically conductive material on the tip end prior to the step of providing the insulating material.

3. The process of claim 1, wherein the step of deforming the first and second layers of the nickel alloy about the perimeter to fully encapsulate the layer of copper or copper alloy comprises a coining process.

* * * * *

UNITED STATES PATENT AND TRADEMARK OFFICE
CERTIFICATE OF CORRECTION

PATENT NO.    : 6,298,550 B1
DATED         : October 9, 2001
INVENTOR(S)   : Lawrence T. Kirwan, Jr.

It is certified that error appears in the above-identified patent and that said Letters Patent is hereby corrected as shown below:

Column 1,
Line 10, "and is a Division" should read -- and under --.

Signed and Sealed this

Twenty-third Day of April, 2002

Attest:

Attesting Officer

JAMES E. ROGAN
Director of the United States Patent and Trademark Office